United States Patent [19]
Nelson et al.

[11] Patent Number: 5,980,927
[45] Date of Patent: Nov. 9, 1999

[54] METHOD AND APPARATUS FOR ADMINISTERING ANALGESICS, AND METHOD FOR MAKING SAME DEVICE

[75] Inventors: Timothy S. Nelson, Elk River; Matthew A. Bergan, Brooklyn Park, both of Minn.

[73] Assignee: Medtronic, Inc., Minneapolis, Minn.

[21] Appl. No.: 08/775,528

[22] Filed: Jan. 2, 1997

Related U.S. Application Data

[63] Continuation of application No. 08/386,853, Feb. 10, 1995, abandoned.

[51] Int. Cl.⁶ .................. A61F 2/02; A61K 9/22; A61K 47/30
[52] U.S. Cl. .............. 424/425; 424/423; 424/424; 424/426; 604/890.1; 514/772.3
[58] Field of Search .................. 424/426, 423, 424/424, 425; 604/890.1; 514/772.3

[56] References Cited

U.S. PATENT DOCUMENTS

| | | | |
|---|---|---|---|
| 4,346,709 | 8/1982 | Schmitt | 128/260 |
| 4,774,091 | 9/1988 | Yamahira et al. | 424/426 |
| 4,892,538 | 1/1990 | Patrick et al. | 604/891.1 |
| 5,180,716 | 1/1993 | Yaksh et al. | 514/58 |
| 5,330,768 | 7/1994 | Park et al. | 424/501 |
| 5,487,739 | 1/1996 | Aebischer et al. | 604/890.1 |

FOREIGN PATENT DOCUMENTS

WO 94/01166  1/1994  WIPO .................. A61M 31/00

OTHER PUBLICATIONS

"Controlled Releases of ACNU For Brain Tumor and Of Morphine For Anesthesia," I. Kaetsu, et al., *Proceed. Intern. Symp. Control. Rel. Bioact. Mater.* 21:527–8 (1994).

"Biodegradable Polymers For Controlled Delivery of Chemotherapy With and Without Radiation Therapy in the Monkey Brain", by Henry Brem, M.D. et al., in J. Neurosurg., Feb. 1994, vol. 80, pp. 283–290.

"Interstitial Taxol Delivered from a Biodegradable Polymer Implant against Experimental Malignant Glioma", by Kevin A. Walter et al., in Cancer Research, Apr. 15, 1994, vol. 54, pp. 2207–2212.

*Primary Examiner*—Carlos A. Azpuru

[57] ABSTRACT

A device and method is disclosed for continuously administering an analgesic to the neuraxis of an organism. The device comprises a polymeric matrix body loaded with the analgesic. The body is implanted in the neuraxis where the analgesic diffuses into the neuraxis.

61 Claims, 5 Drawing Sheets

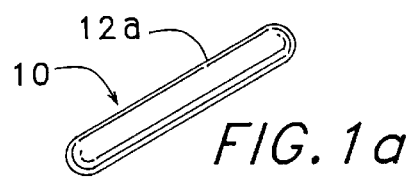
FIG. 1a
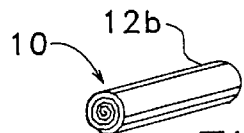
FIG. 1b
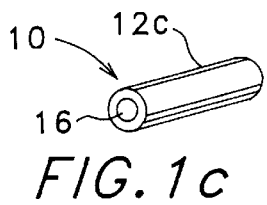
FIG. 1c
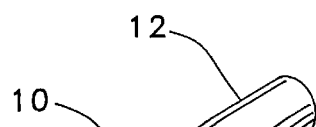
FIG. 1
FIG. 2
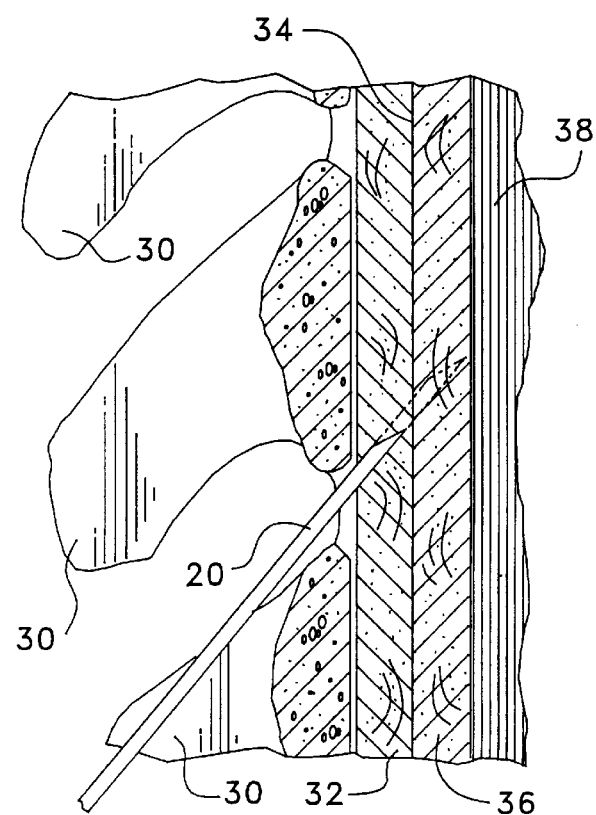
FIG. 3

METHOD AND APPARATUS FOR ADMINISTERING ANALGESICS, AND METHOD FOR MAKING SAME DEVICE

This application is a continuation of application(s) Ser. No. 08/386,853 filed on Feb. 10, 1995, now abandoned.

TECHNICAL FIELD

This invention relates to a device and method for administering analgesics to the neuraxis of an organism. More specifically, this invention relates to the long term release of an analgesic from a biocompatible polymeric matrix device implanted into the central nervous system of a human patient or other warm blooded animal.

BACKGROUND OF THE INVENTION

Constant or chronic pain is a significant medical problem, for example in terminal cancer patients. Many of the drugs, such as the opioid class of analgesics, used to treat severe chronic pain act on receptors found in the neuraxis. By "neuraxis" as used herein is meant any region of tissue that comprises the spinal cord, brain or central nervous system.

The current regimen for treatment of these patients is systemic administration of relatively high doses of analgesics by for example oral, subcutaneous, intramuscular, intravenous and related routes on a daily or continuous basis. Oral administration of an analgesic is problematic because the patient experiences high systemic concentration of drug at the time of ingestion followed by a gradual decrease in systemic concentration of the drug until the next dose is ingested. Other methods of systemic administration are problematic because they may be invasive, for example placement of an intravenous catheter for continuous administration of the analgesic. In either case, however, the analgesic is distributed equally throughout the body after being administered systemically and diffuses across the blood-brain barrier into the neuraxis to its central site of action, blocking pain messages to the brain. The cost for treating these patients is high from a hospital care as well as from a pharmaceutical standpoint since many patients must be maintained in the hospital to continue their pain treatment regimen of high doses of the analgesic. Furthermore, side effects related to the systemic administration of high doses of, for example, opioids include sedation, respiratory depression, nausea, constipation and vomiting. These side effects are well documented in product labeling and the literature and detract greatly from the already compromised quality of life of these patients.

More recently, transdermal patches have been developed as a means for efficiently delivering analgesics to patients on a continuous basis. A patch is loaded with an analgesic such as fentanyl and is attached to the patient's skin by means of typically an adhesive. The analgesic diffuses out of the patch and crosses the patient's skin, where it is absorbed by the body. Patients may be required to wear a number of patches to obtain adequate therapeutic response, as the analgesic site of action is in the neuraxis. While less invasive than other administration techniques listed above, systemic side effects resulting from high levels of analgesic in the body are still a significant medical problem and continue to compromise patient quality of life.

Alternatively, spinal administration (intrathecal or epidural) of centrally acting analgesics via an externalized spinal catheter, a spinal catheter connected to an external infusion pump, a spinal catheter connected to a fully implanted infusion pump and other related systems has been shown to be therapeutically effective for the treatment of chronic pain. To reduce systemic side effects caused by relatively high dosage systemic delivery, direct spinal delivery of the analgesic is preferred. In this way, drug is delivered in a concentrated manner and at low doses to its specific site of action on receptors in the neuraxis, minimizing systemic side effects as outlined above. Spinal catheter placement and infusion pump use, while shown to be highly effective, represent a therapy alternative that is relatively expensive and invasive to implant. These therapies also present with risk of spinal infection such as meningitis since the blood-brain barrier has been compromised and drug is delivered to the neuraxis from an external source such as a drug pump.

Recent research has also demonstrated that living cells that produce natural analgesics can be encapsulated into a silicone sheath and implanted into the central nervous system. It has not been established whether these cells produce therapeutic quantities of analgesics while in vivo or how long the encapsulated cells will remain viable. Doses of analgesic that the cells produce in many instances can not be controlled and external stimuli, for example nicotine, may change cell viability parameters. Finally, potential for infection in the neuraxis if one of these modules were to rupture has not been characterized.

The present invention provides an alternative means for achieving continuous central nervous system administration of an analgesic into the neuraxis via intraventricular, epidural, intrathecal and related routes for those suffering chronic pain and is directed to solving one or more of the problems noted above. The invention comprises an analgesic carrying device and its method of use, including implantation, which releases the analgesic in a continuous and sustained-release manner. The device consists of a biocompatible polymer matrix body loaded with an analgesic such that a slow, preferably constant release of the analgesic is provided. The polymer matrix substrate may be constructed of any of a number of biostable or biodegradable polymers that act as the carrier matrix for the analgesic. Ideally, therapeutic levels of the analgesic will be delivered over the long term, i.e., one month to one year. Two preferred analgesics are fentanyl and sufentanil, opioids about 100 to 500 and 1000 to 5000 times, respectively, more potent than morphine. Preferably the method of the invention administers the analgesic intraventricularly, intrathecally, epidurally, or by other related routes to the neuraxis. The intrathecal route of administration is preferred.

SUMMARY OF THE INVENTION

With this invention it is recognized for the first time that increased cost-effectiveness and simplicity of the administration of analgesics directly to the central nervous system, i.e., neuraxially, may be accomplished by means of a polymer matrix body loaded with an analgesic and made available for diffusion from the matrix into the biologic neuraxial environment.

BRIEF DESCRIPTION OF THE FIGURES

FIG. 1 is a view of a side matrix body made from a biocompatible polymer containing analgesic in the interstices thereof.

FIGS. 1a, 1b and 1c show alternate configurations.

FIG. 2 is a view of a preferred shape of the matrix body for retrieval purposes.

FIG. 3 is a schematic showing the spinal column and demonstrating the lumbar implantation of an analgesic loaded matrix body by ejection of same from a needle.

DETAILED DESCRIPTION OF THE INVENTION

Figure 4:
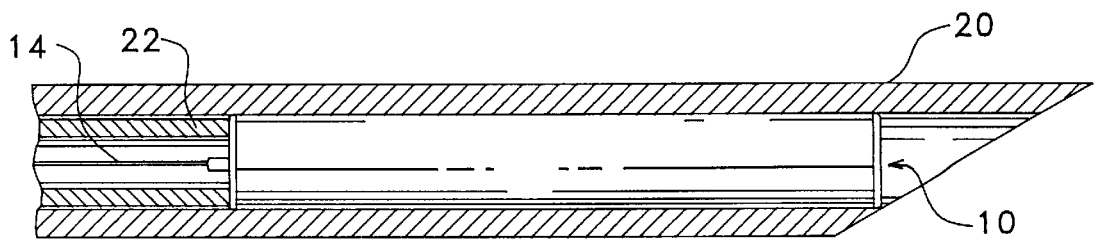
FIG. 4 is a more detailed showing of the matrix body in the needle of FIG. 3 and a method of delivery of same into the body environment.

Turning now to the drawings, which disclose examples of various drug delivery devices and methods according to the invention, one embodiment of the device is indicated in FIG. 1 at 10. Device 10 comprises a polymeric matrix body 12 made of a biostable or biodegradable polymer loaded with an analgesic such as fentanyl. Device 10 can be used for the continuous administration of the analgesic to the neuraxis of an animal body. Device 10 delivers an analgesic by elution of the analgesic from the matrix polymer body 12 in a fluid environment at a gradual manner with the drug being delivered at a controlled and continuous rate over a prolonged period of time. The analgesic elutes from the matrix body 12 due to the permeation of water and lipids from the interstitial fluid through the polymer matrix. This permeation solubilizes the analgesic to allow release from the matrix body 12. Various factors such as geometry, size, material, and pore size all affect permeability of the polymer matrix body 12 and resultant elution rates of the analgesic to the neuraxis.

FIG. 1a shows a cylinder configuration for body 12a of device 10 with rounded ends for easing placement and retrieval. FIG. 1b shows a cylinder configuration for body 12b of device 10 formed from a rolled-up sheet of polymer material. FIG. 1c shows a cylinder configuration for body 12c of device 10 in the form of a hollow tube, containing a quantity of an analgesic 16. The analgesic 16 may be dispersed within the polymer. Many other configurations will be apparent to those familiar with this art.

Attached to body 12 by any suitable means of connection such as adhesive or fusion is a tether 14 of such a length as to allow for retrieval of device 10 at any time following implantation thereof into the neuraxis region of an animal body. The tether 14 may be of any known biocompatible material such as nylon as is generally used in surgery.

FIG. 2 illustrates a preferred configuration of body 12 in which the proximal end thereof, i.e., the end to which tether 14 is attached is tapered for facilitating retrieval.

The polymer utilized for making up the matrix body 12 of device 10 may be any suitable biocompatible polymer, whether biostable or biodegradable.

Biostable polymers that may be utilized include silicone, polyurethane, polyether urethane, polyether urethane urea, polyamide, polyacetal, polyester, poly ethylene-chlorotrifluoroethylene, poly tetrafluoroethylene (PTFE or "Teflon®"), styrene butadiene rubber, polyethylene, polypropylene, polyphenylene oxide-polystyrene, poly-a-chloro-p-xylene, polymethylpentene, polysulfone and other related biostable polymers. Presently, polyurethane is a preferred biostable polymeric matrix material for body 12, but many of the above listed polymers may be useful for this application.

Biodegradable polymers that may be utilized include polyanhydrides, cyclodestrans, poly lactic-glycolic acid, polyorthoesters, n-vinyl alcohol, polyethylene oxide/polyethylene terephthalate, polyglycolic acid, polylactic acid and other related bioabsorbable polymers. In the event a biodegradable polymer is used as the matrix body 12, the tether 14 may or may not be utilized since permanent implantation may be acceptable.

The analgesic 16 loaded into the polymer matrix body 12 may be from one of any number of classes of analgesics that have been shown to act centrally on specific pain receptors in the neuraxis. Potential drug classes include analgesics, typically called opioids, that act on opioid pain receptors. Examples of such opioid analgesics are morphine, fentanyl, sufentanil, alfentanil, hydromorphone, meperidine, methadone, buprenorphine, DADL, butorphanol and related opioids. Other potential drug classes include analgesics that act on non-opioid pain receptors. One such group of analgesics that act on non-opioid pain receptors are alpha-2 adrenergic receptor agonists such as clonidine, tizanidine, ST-91, medetomidine, dexmedetomidine and related alpha-2 adrenergic agonists. Another group of analgesics are NMDA receptor antagonists such as dexmethorphan, Ifenprodil, MK-801 and related NMDA antagonists. Yet another group of analgesics are somatostatin analogs such as Octreotide, Sandostatin, Vapreotide, Lanreotide and related somatostatin analogs. Finally, other analgesics may be used that act on non-opioid pain receptors such as ketorolac, super oxide dismutase, baclofen, calcitonin, serotonin, vasoactive intestinal polypeptide, bombesin, omega-conopeptides and related non-opioid analgesics. The list is not intended to be complete, but rather to demonstrate the broad potential and feasibility of the invention to act on a number of central pain receptors, even though not all agents may be readily used to construct a device of clinically viable size. The preferred analgesic presently is the opioid fentanyl that is about 100 to 500 times more potent than morphine and is well characterized in the neuraxis or alternatively sufentanil that is about 1000 to 5000 times more potent than morphine.

Analgesic Loading

The analgesic 16 may be loaded into the polymer matrix body 12 by a number of techniques. The choice of loading technique for a particular analgesic/polymer matrix/device geometry will be dependent on a number of factors including drug/polymer/solvent compatibility, desired final concentration of analgesic 16 in the polymer matrix body 12, simplicity of the process, desired final geometry of the device 10 and preferred elution characteristics of the completed device 10. As examples, a few loading technique options are listed as follows. The list is not intended to be complete or limiting, but rather to serve as examples well understood by anyone skilled in the art.

The analgesic 16 may be loaded into the polymer body 12 by means of dispersion loading. Dispersion loading is the technique of loading a powdered substance into a polymer by stir-mixing it into the polymer precure or solution to make a dispersion of the two materials. The powder is not dissolved by the polymer solution in dispersion loading. The polymer is solidified by curing or solvent evaporation and a homogeneous blend of analgesic 16 in the polymer is achieved. The analgesic 16 has not reacted with the polymer, but rather is dispersed within the interstitial spaces of the cured polymer. The concentration of drug that can be loaded into the polymer is limited only by the physical integrity of the resulting polymer matrix body 12. Dispersion mixing is a standard technique for loading dexamethasone into polymeric lead tips to create steroid eluting leads.

The dispersion loading method is the preferred method of combining analgesic 16 with the polymeric matrix body 12 because the method allows for a fairly high percentage of analgesic 16 to be added to the polymer to form matrix body 12. The percentage of analgesic 16 added to the polymer to form matrix body 12 is preferably from 10% to 80% by weight. This percentage has been found to maintain the integrity of the polymer substrate in body 12. A higher loading concentration of analgesic 16 allows for the design of a smaller device 10 for clinical use and placement in the neuraxis.

The dispersion loading method also allows the body 12 to be formed into optimal geometries prior to cure of the polymer or for body 12 to be extruded as a tube or other geometry. Finally, solvent compatibility between the polymer of body 12 and the analgesic 16 is not a factor.

Alternatively, solvent swelling can be used to combine the analgesic 16 with the polymeric matrix body 12. This method is particularly useful where a preformed polymer body 12 is introduced into a solution of the analgesic 16 in a solvent that acts as a swelling agent for the polymer body 12. The body 12, while swelling, absorbs the solvent along with the dissolved analgesic 16 until a steady state is achieved. The polymer body 12 is then allowed to dry with the solvent evaporating from the sample and the analgesic 16 left behind in the body 12. As the body 12 dries, it returns from its swelled state to its original geometry and size. Solubility of the analgesic 16 in the solution limits the possible concentration of drug that can be introduced by this technique. Even so, the technique is well known and has been used successfully to load antimicrobials into polymer matrices. (See, for example, U.S. Pat. No. 4,917,686).

Solution loading is similar to dispersion loading except that the analgesic 16 or drug must be soluble in the polymer solvent. The cured polymer body 12 then includes the dissolved analgesic 16 or drug in its matrix.

Finally, the method of reservoir loading may be used to combine the analgesic 16 with the body 12. This method comprises loading pure drug or analgesic 16 inside a hollow tube and sealing the ends of the tube to form the body 12. The analgesic 16 then diffuses through the polymer tubing wall of body 12.

Although the configuration of the device 10 may be varied including for example rods, rolled up sheets, buttons, discs, tubes, microspheres and fibers, the presently preferred configuration is a small tube or rod of polymer the size and shape of a grain of rice which may be readily introduced into the intrathecal space via a 14 gauge needle. Final product configuration may be fabricated by any of the foregoing techniques.

More specifically, small device sizes typically less than 0.10 inches in diameter are contemplated for the preferred method of administration comprising the simple lumbar puncture technique. This technique is illustrated with reference to FIG. 3 wherein a needle 20, preferably fourteen (14) gauge or smaller in size is inserted between the vertebrae 30 into the epidural space 32 or the intrathecal space 36 in the known lumbar puncture technique. The arachnoid layer is shown at 34 and the spinal cord at 38.

Needle 20, as is best shown in FIG. 4, contains the device 10 to be implanted. Needle 20 also contains a pusher rod or cylinder 22 that is used to eject device 10 from needle 20 for implantation. Preferably, as shown, pusher rod or cylinder 22 is hollow so as to readily accommodate tether 14 where-upon removal of needle 20 and pusher rod 22 leaves the implanted device 10 in place with the tether 14 extending therefrom. Tether 14 preferably extends away from the body 10 and terminates under the skin but outside the spinal cord so that tether 14 is easily accessible when retrieval is desired. To retrieve body 12, the needle 20 is simply inserted over the tether 14 and moved to body 12. Tether 14 is then used to draw the body 12 into the needle 20 and the body 12 is removed with the needle 20.

Alternatively, the combined analgesic/polymer matrix body 12 may be attached to the end of a standard spinal catheter by any suitable means such that the outer diameter of the device 10 equals the outer diameter of the catheter. The device/catheter system may then be introduced into the desired location in the spinal column by the standard lumbar puncture technique using standard needles and procedures. The system may be retrieved in the same manner as a standard spinal catheter is retrieved today as is well understood by those skilled in the art.

Preferably, implantation of the device 10 will occur in the intrathecal space as opposed to the epidural space. This is because less analgesic 16 is required for effective control of chronic pain when device 10 is introduced to the intrathecal space as compared to the epidural space. As already indicated, the techniques described herein may also be used for implantation of device 10 into a brain ventricle.

Table I shown hereinbelow provides an example of the device size requirements for providing a minimal six-month dose of fentanyl to accomplish chronic pain control in a more or less typical situation involving intrathecal administration.

TABLE I

DRUG NEEDS

Intrathecal fentanyl dosage: 0.1 to 0.3 mg/day
Using minimal dose for 6 months
Assuming polymer and drug densities ≈ 1 g/cm$^3$ or 1 mg/mm$^3$
0.1 mg/day × 180 days × 1 mm$^3$/mg = 18.0 mm$^3$ fentanyl to be delivered

DEVICE SIZE

Assume 20% loading, and 50% delivery in 6 months $$\frac{1.80 \text{ mm}^3 \text{ of active fentanyl}}{0.1 \text{ mm}^3 \text{ actives/mm}^3 \text{ inactives}} = 180.0 \text{ mm}^3 \text{ of device}$$

Device of volume 180.0 mm$^3$ or 0.18 cm$^3$:

Cube, 0.56 cm on-a-side
Cylinder, D = 1.8 mm, L = 70 mm (2.8 in)

DETAILED DESCRIPTION OF EXAMPLES

The following examples are set forth as representative of the spirit of the present invention. These examples are not to be construed as limiting the scope of the invention, as these and other functionally equivalent methods and devices will be readily apparent to those skilled in the art. Studies to date have focused on developing and characterizing a feasible polymer matrix substrate for body 12 that will elute analgesic 16 continuously and over the long term, i.e., one month to one year. In patients or animals, near zero order release kinetics for the duration of the implant are preferred because stable drug concentrations may be maintained in the neuraxis. Zero order release kinetics means that over time, the amount of drug released by the polymer matrix remains at a relatively constant rate. For example, for an implant having a useful duration of several months, with zero order release kinetics, the amount of drug released from the polymer matrix on day 30 will be the same as the amount of drug released from the matrix on day 5. Finally, the analgesic loaded polymer matrix body 12 must be sterilizable, biocompatible and of a geometry and size that is easily implantable and removable in the neuraxis.

For the following examples, fentanyl citrate was chosen as the preferred analgesic 16 because it has a centrally acting mode of effect, is 100 times more potent than morphine, and is a stable and well characterized opioid analgesic. Fentanyl citrate powder was purchased from USPC Inc., Rockville, Md. Polymer substrate materials tested included medical grade silicone purchased from Rehau Corp., Leesburg, Va., Trade name Raumedic SI2000) and Pellethane brand polyurethane of durometer 80A purchased from Dow Chemical, Midland, Mich. Polyurethane adhesive was prepared by heat press molding Pellethane pellets into film and dissolving the film in dimethyl acetamide (DMAC) solvent.

Initial studies identified a polymer matrix, developed an effective technique for loading fentanyl into the matrix as discussed earlier, and compared the in vitro release kinetics of fentanyl from various matrices. Also described are studies comparing the effect of fentanyl release as a function of polymer type, matrix porosity, drug concentration and device shape. All samples were placed into a phosphate buffered saline solution and were maintained at 37 C. Eluate samples were pulled at various time points for analysis by standard high pressure liquid chromatography (HPLC) techniques, with samples being compared against a standard fentanyl concentration curve. Examples are discussed as follows:

EXAMPLE 1

Figure 5:
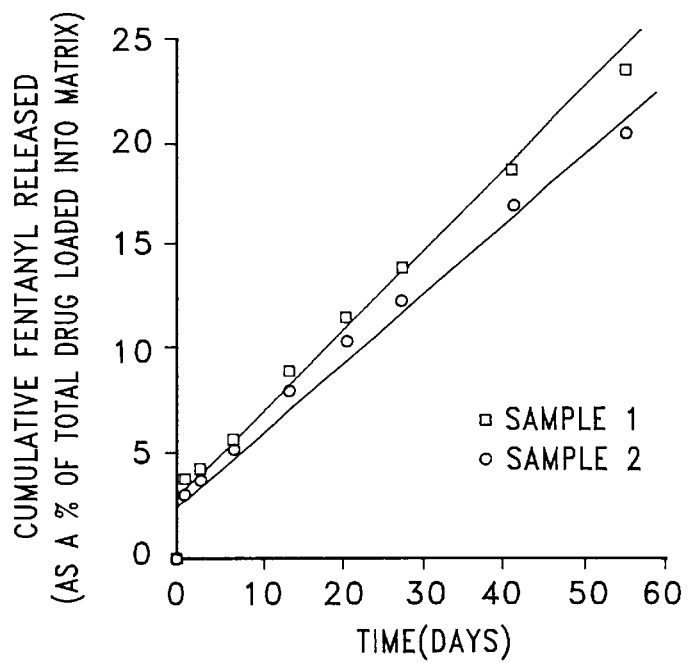
FIG. 5 is a graph showing examples of fentanyl elution from polyurethane over time as the percent of the total fentanyl available.

This example evaluates the release kinetics of the analgesic fentanyl from relatively nonporous polyurethane matrix samples 1 and 2 over time. Data is shown in FIG. 5. The samples 1 and 2 are also compared to alternative silicone carrier matrix samples 3 and 4 shown in FIG. 6 and discussed in Example 2.

Polyurethane samples 1 and 2 in FIG. 5 were prepared by the dispersion technique discussed earlier and well understood by those skilled in the art. Polyurethane used was Pellethane 80A. Samples 1 and 2 were loaded with a 10% fentanyl powder and were prepared in a film configuration approximately three quarter inches long by one quarter inch wide by 0.015 inches thick. Samples 1 and 2 were placed in standard phosphate buffered solution (PBS) and allowed to elute drug for 60 days at 37C.

FIG. 5 shows the amount of fentanyl delivered as a percent of the total amount of fentanyl loaded into the sample, i.e., cumulative elution. Release kinetics are nearly zero order, with the amount of drug being delivered on day 50 nearly equal to the amount of drug being delivered on day 10.

Figure 7:
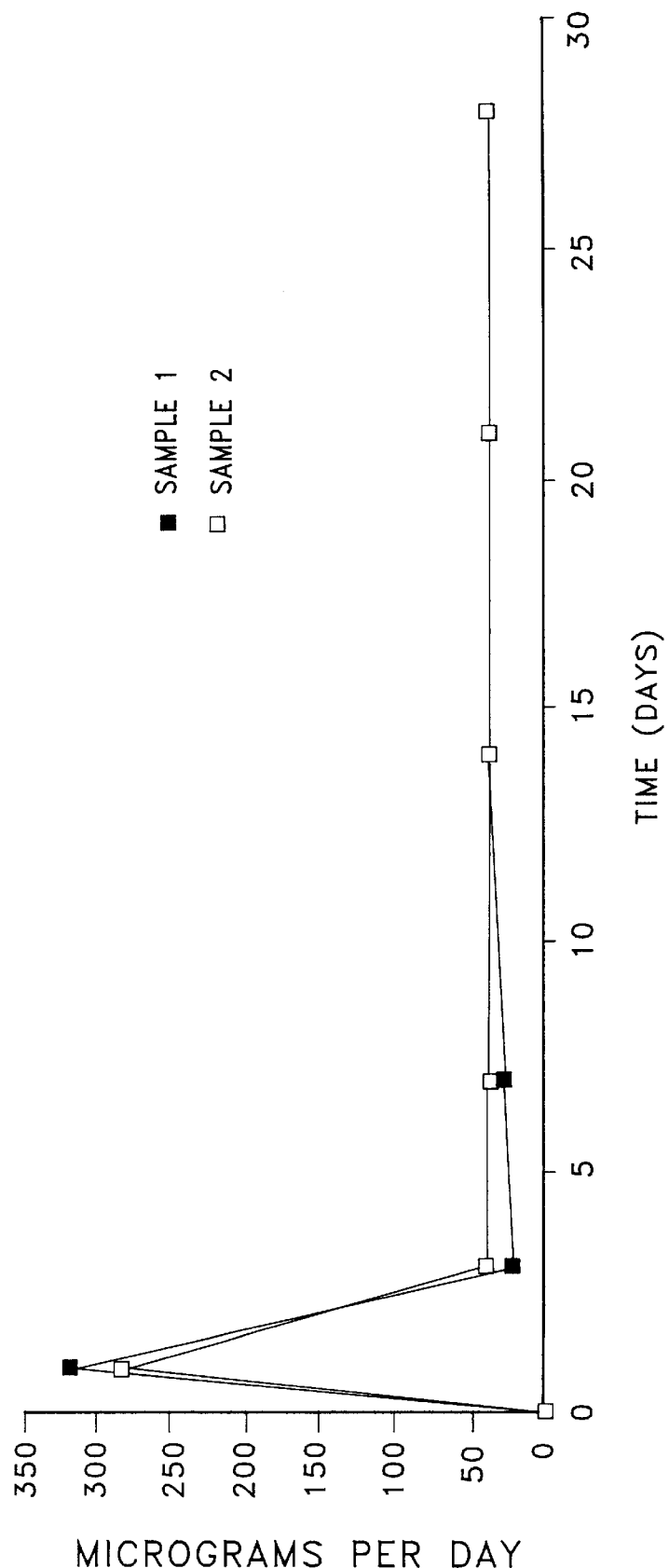
FIG. 7 is a graph showing sample matrices in terms of effective dose in micrograms per day as administered from a matrix body according to the invention.

FIG. 7 presents the data for the first 28 days as micrograms per day of fentanyl delivered from the matrix by samples 1 and 2. Following a first day bolus, the samples both eluted drug at approximately 30 micrograms per day, approximately one third to one tenth the effective intrathecal dose required for human clinical use. Results for both samples were consistent for each time point as well as over time.

EXAMPLE 2

This example evaluates the release kinetics of the analgesic fentanyl from silicone matrix samples 3 and 4 over time. The samples 3 and 4 were also compared to alternative polyurethane carrier material samples 1 and 2 as described in Example 1 above.

Figure 6:
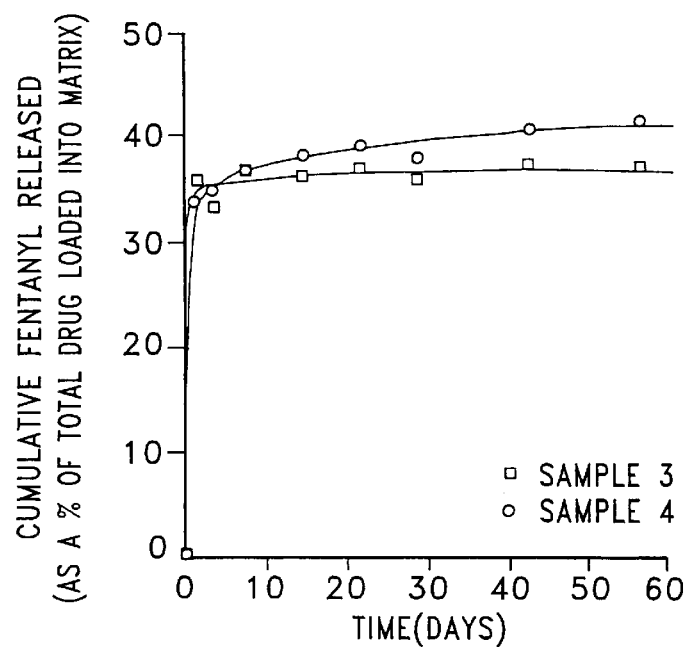
FIG. 6 is a graph showing fentanyl elution from silicone over time as the percent of the total fentanyl available.

Silicone samples 3 and 4 in FIG. 6 were prepared by the dispersion technique discussed earlier and well understood by those skilled in the art. Samples 3 and 4 were loaded with a 10% fentanyl powder and were prepared in a film configuration approximately one inch long by one half inch wide by 0.020 inches thick. Samples were placed in standard phosphate buffered solution (PBS) and allowed to elute drug for 60 days at 37 C.

FIG. 6 shows the amount of fentanyl delivered as a percent of the initial total amount of fentanyl loaded into the sample, i.e., cumulative elution. In contrast to the polyurethane samples 1 and 2, silicone samples 3 and 4 provide a bolus release of fentanyl on day one followed by decreasing drug release thereafter. Results of both silicone samples 3 and 4 were consistent for each time point as well as over time.

EXAMPLE 3

This example compares the effect of different fentanyl loading concentrations on release kinetics using a relatively nonporous polyurethane film.

Figure 8:
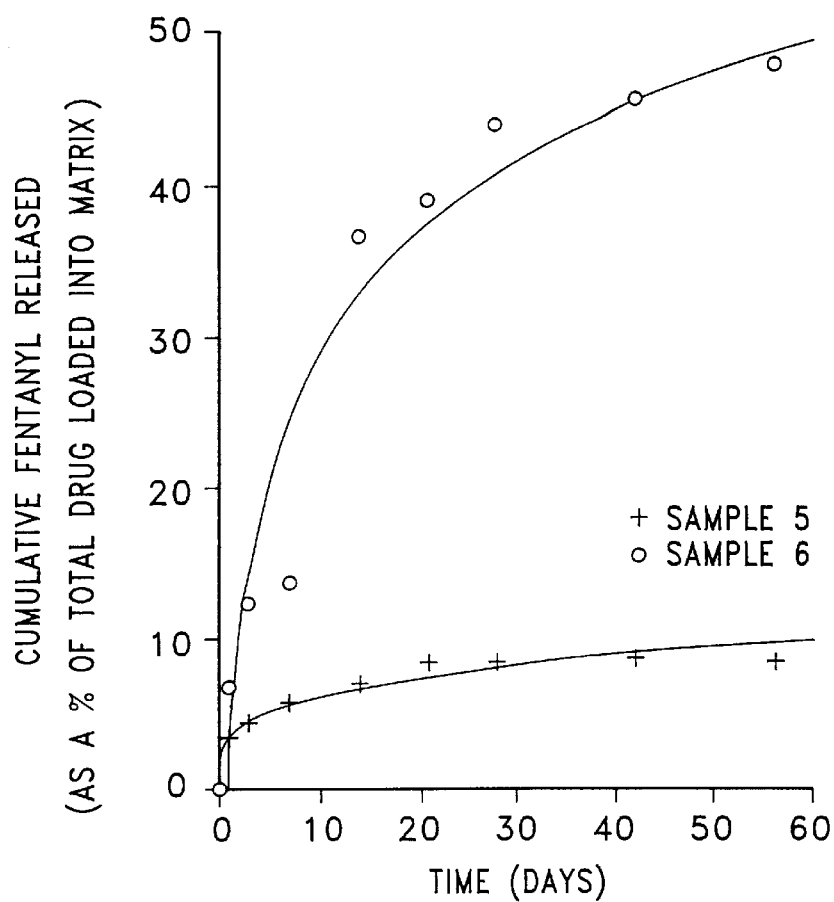
FIGS. 8, 9 and 10 are graphs showing the amount of fentanyl delivered as a percent of the total amount of fentanyl bonded with several sample matrix geometries.

Polyurethane samples 5 and 6 in FIG. 8 were prepared by the dispersion technique discussed earlier. Polyurethane used was Pellethane 80A. Samples 5 and 6 were loaded with 10% fentanyl powder and 25% fentanyl powder, respectively by weight and prepared in a film configuration approximately one quarter inch wide by one quarter inch long by 0.01 inches thick. Samples 5 and 6 were placed in standard phosphate buffered solution (PBS) and allowed to elute drug for 60 days at 37 C.

FIG. 8 shows the cumulative amount of fentanyl delivered as a percent of the total amount of fentanyl loaded into the samples. The graph shows that the higher the concentration of fentanyl loaded into the sample, the greater the release rate of the analgesic. The 25% fentanyl loaded sample 6 exhibits nearly zero order release kinetics over the first 30 days, with drug elution rates tailing off from day 30 to day 60.

EXAMPLE 4

This example compares release kinetics of a number of fentanyl loading concentrations from a relatively porous polyurethane pellet.

Figure 9:
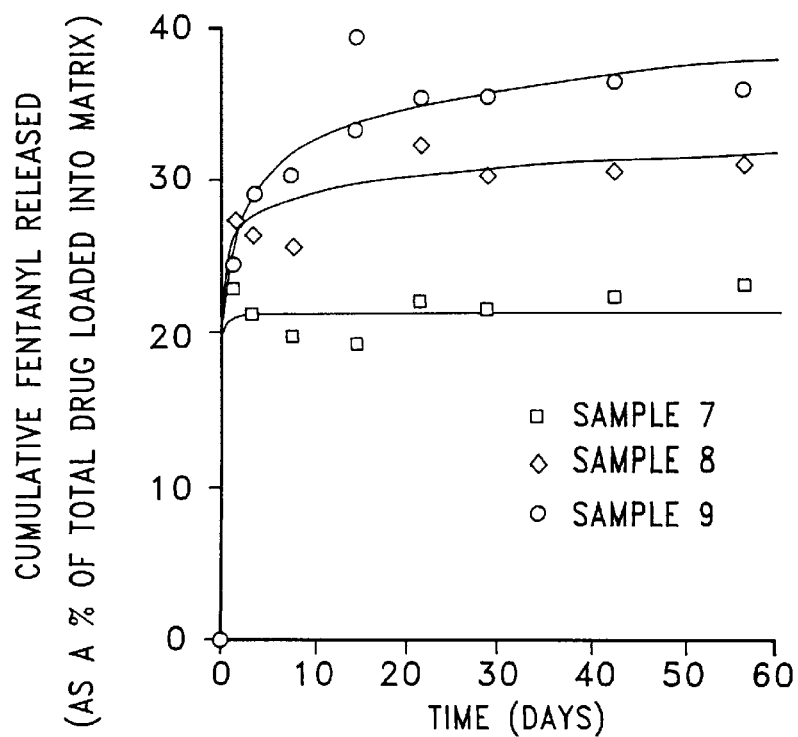

Polyurethane samples 7, 8 and 9 in FIG. 9 were prepared by the dispersion technique discussed earlier. Polyurethane used was Pellethane 80A as in the previous examples, but the polymer samples were allowed to cure in a high humidity environment rather than in a vacuum. Casting the polyurethane film in a high humidity environment created a phase inversion allowing the polyurethane to precipitate and cure in a relatively porous fashion. Samples 7, 8 and 9 were loaded with 10% fentanyl powder, 25% fentanyl powder, and 40% fentanyl powder, respectively by weight, and were prepared as pellets approximately one half inch long by 0.05 inches wide by 0.03 inches thick. The samples were placed in standard phosphate buffered solution and allowed to elute drug for 60 days at 37 C.

FIG. 9 shows the amount of fentanyl delivered as a percent of the total amount of fentanyl loaded into the samples. The graph shows that the higher the concentration of drug loaded into the sample, the greater the release rate. All samples suggest a large analgesic bolus is delivered on day one, followed by decreasing analgesic elution thereafter.

EXAMPLE 5

This example compares effects of geometry of a sample on release kinetics. Polymer matrix material and fentanyl loading concentration are held constant.

Figure 10:
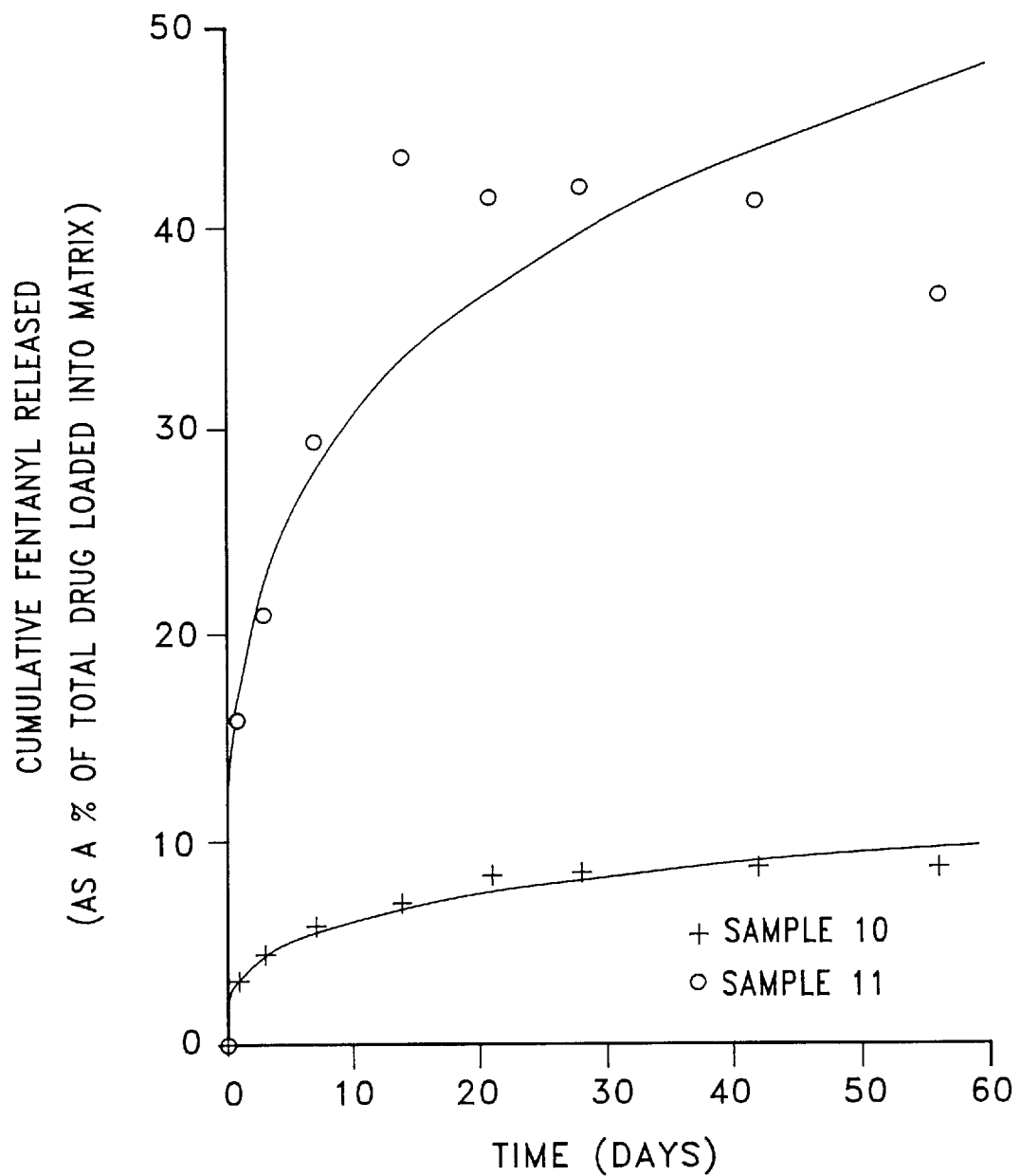

Polyurethane samples 10 and 11 in FIG. 10 were prepared by the dispersion technique discussed earlier. Polyurethane used was Pellethane 80A. Samples 10 and 11 ere loaded with 10% fentanyl powder and were prepared as a film and a tube, respectively. Tubing sample 11 was prepared approximately one eighth inches in outer diameter with a wall thickness of 0.005 inches and one quarter inch in length. Film sample 10 was prepared approximately one quarter inch wide by one quarter inch long by 0.01 inches thick. Samples 10 and 11 were placed in standard phosphate buffered solution and allowed to elute drug for 60 days at 37C.

FIG. 10 shows the amount of fentanyl delivered as a percent of the total amount of fentanyl loaded into the samples. The samples provide consistent drug release over 60 days, with the tube geometry releasing a greater amount of fentanyl and at a greater rate.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. The examples demonstrate that an optimum geometry and analgesic loading may be prepared to allow for nearly zero order release kinetics (straight line) of therapeutic amounts of an analgesic over a period of time, for example one month to one year.

What is claimed is as follows:

1. A method for administering an analgesic to an animal comprising the steps of:
    implanting, in the region of the spinal column of the animal, a biostable polymeric matrix body loaded with the analgesic wherein said analgesic is only released from said biostable polymeric matrix, and
    releasing an efficacious amount of the analgesic over time to the animal from the matrix body.

2. The method of claim 1 wherein the step of releasing includes eluting the analgesic at a nearly constant rate over the useful life of the analgesic.

3. The method of claim 1 wherein the analgesic released in the step of releasing is an analgesic that acts on opioid pain receptors.

4. The method of claim 3 wherein the analgesic that acts on opioid pain receptors is selected from the group consisting of morphine, fentanyl, sufentanil, alfentanil, hydromorphone, meperidine, methadone, buprenorphine, DADL and butorphanol.

5. The method of claim 1 wherein the analgesic released in the step of releasing is an analgesic that acts on opiod pain receptors.

6. The method of claim 5 wherein the analgesic that acts on non-opioid pain receptors is selected from the group consisting of ketorolac, super oxide dismutase, baclofen, calcitonin, serotonin, vasoactive intestinal polypeptide, bombesin and omega-conopeptide.

7. The method of claim 1 wherein the analgesic released in the step of releasing is an alpha-2 adrenergic agonist.

8. The method of claim 7 wherein the alpha-2 adrenergic agonist is selected from the group consisting of clonidine, tizanidine, ST-91, medetomidine and dexmedetomidine.

9. The method of claim 5 wherein the analgesic that acts on non-opioid pain receptors is an NMDA receptor antagonist.

10. The method of claim 9 wherein the NMDA receptor antagonist is selected from the group consisting of dexmethorphan, Ifenprodil and MK-801.

11. The method of claim 5 wherein the analgesic that acts on non-opioid pain receptors is a somatostatin analog.

12. The method of claim 11 wherein the somatostatin analog is selected from the group consisting of Octreotide, Sandostatin, Vapreotide and Lanreotide.

13. The method of claim 1 wherein the step of implanting a biostable polymeric matrix body loaded with an analgesic includes implanting a polymeric matrix body made of a material chosen from the group consisting of silicone, polyurethane, polyether urethane, polyether urethane urea, polyamide, polyacetal, polyester, poly(ethylene-chlorotrifluoroethylene), poly tetrafluoroethylene (Teflon), styrene butadiene rubber, polyethylene, polypropylene, polyphenylene oxide-polystyrene, poly-a-chloro-p-xylene, polymethylpentene and polysulfone.

14. The method of claim 1 further comprising the step of configuring the body for ease of introduction to and removal from the spinal column of an animal prior to performing the step of implanting a biostable polymeric matrix body.

15. The method of claim 1 further comprising the step of attaching a tether to the matrix body to facilitate removal of the matrix body from the animal, and, wherein the step of implanting a biostable polymeric matrix body includes implanting the matrix body so that the tether extends away from the polymeric matrix body and terminates outside the spinal column of the animal so that the tether is easily accessible when retrieval is desired.

16. The method of claim 1 wherein the step of implanting a biostable polymeric matrix body loaded with the analgesic includes the steps of:
    placing the matrix body in a hollow needle; and
    pushing the matrix body through and out of the needle with a pusher rod.

17. The method of claim 1 wherein the step of implanting a biostable polymeric matrix body loaded with the analgesic includes the steps of:
    attaching the matrix body to the distal end of a catheter; and
    introducing the distal end of the catheter into the spinal column.

18. The method of claim 1 wherein the step of implanting a biostable polymeric matrix body further comprises the step of implanting a biostable polymeric matrix body in the spinal column using a lumbar puncture technique.

19. The method of claim 1 wherein the matrix body is implanted in the intrathecal space.

20. The method of claim 1 wherein the matrix body is implanted in the epidural space.

21. The method of claim 1 wherein the step of implanting a biostable polymeric matrix body loaded with the analgesic includes the step of placing the analgesic in the matrix body in an amount of about 10% to 80% by weight.

22. A method for administering an analgesic to an animal comprising the steps of:
    making a biostable polymeric matrix body loaded with an analgesic, the matrix body configured for ease of introduction to and removal from the spinal column of the animal;
    implanting, in the region of the spinal column of the animal; and diffusing an efficacious amount of the analgesic over time to the animal from the matrix body, wherein the analgesic is diffused at a sustained rate over the useful life of the analgesic.

23. The method of claim 22 wherein the step of making a biostable polymeric matrix body loaded with an analgesic includes the step of loading the analgesic into the matrix body by means of dispersion loading.

24. The method of claim 22 wherein the step of making a biostable polymeric matrix body loaded with an analgesic includes the step of loading the analgesic into the matrix body by means of solvent swelling.

25. The method of claim 22 wherein the step of making a biostable polymeric matrix body loaded with an analgesic includes the step of loading the analgesic into the matrix body by means of solution loading.

26. The method of claim 22 wherein the step of making a biostable polymeric matrix body loaded with an analgesic includes the step of loading the analgesic into the matrix body by means of reservoir loading.

27. A method for making a device to be implanted in the region of the neuraxis of an animal, the device to diffuse analgesic into the region of the neuraxis of the animal at a substantially sustained rate over the life of the device, the method comprising the steps of:

forming a polymeric precure of a biostable material;

stir-mixing a powder mixture of analgesic into the polymeric precure to make a dispersion of the polymeric precure and the analgesic whereby the powder mixture of analgesic is not dissolved by the polymeric precure;

forming the dispersion into a desired configuration; and solidifying the dispersion of the analgesic and polymeric precure.

28. The method of claim 27 wherein the step of solidifying the dispersion is accomplished by curing the dispersion.

29. A method for making a device to be implanted in the region of the neuraxis of an animal, the device to diffuse analgesic into the region of the neuraxis of the animal at a substantially sustained rate over the life of the device, the method comprising the steps of:

a. forming a polymeric substance of a material into a desired configuration;

b. forming a mixture of a solvent and an analgesic;

c. introducing the polymeric substance formed in step a. into the mixture formed in step b.;

d. allowing the polymeric substance formed in step a. to absorb the mixture formed in step b. during the performance of step c.;

e. removing the polymeric substance and absorbed mixture of solvent and analgesic from the mixture of solvent and analgesic after step d. has been performed; and f. drying the polymeric substance and solvent and analgesic mixture removed in step e. so that the solvent evaporates from the polymeric substance and solvent and analgesic mixture thereby leaving only the analgesic absorbed in the polymeric substance.

30. A method for making a device to be implanted in the region of the spinal column of an animal, the device to diffuse analgesic into the region of the spinal column of the animal at a substantially sustained rate over the life of the device, the method comprising the steps of:

a. forming a polymeric substance of a biostable material into a hollow tube, the polymeric material capable of allowing a selected analgesic to diffuse therethrough;

b. loading the selected analgesic into the hollow tube formed in step a.; and c. sealing the ends of the tube formed in step a. with the selected analgesic inside.

31. A device for administering an analgesic to an animal at a sustained rate over a period of time, the device being shaped, sized and adapted for administering the analgesic into the region of the spinal column of the animal, the device comprising:

a biostable polymeric matrix body; and an analgesic, loaded into the matrix body, the analgesic available for diffusion only therefrom into the region of the spinal column of the animal.

32. The device of claim 31 wherein the analgesic is loaded into the matrix body by means of dispersion loading.

33. The device of claim 31 wherein the analgesic is loaded into the matrix body by means of solvent swelling.

34. The device of claim 31 wherein the analgesic is loaded into the matrix body by means of solution loading.

35. The device of claim 31 wherein the analgesic is loaded into the matrix body by means of reservoir loading.

36. The device of claim 31 wherein the matrix body is configured as a rod.

37. The device of claim 34 wherein the matrix body has a diameter of less than about 0.10 inches in diameter.

38. The device of claim 31 wherein the matrix body has a width of less than about 0.10 inches in diameter.

39. The device of claim 31 wherein the matrix body is configured as a rolled up sheet.

40. The device of claim 31 wherein the matrix body is configured as a button.

41. The device of claim 31 wherein the matrix body is configured as a disc.

42. The device of claim 31 wherein the matrix body is configured as a tube.

43. The device of claim 31 wherein the matrix body is configured of a combination of microspheres and fibers.

44. The device of claim 33 wherein the polymeric matrix body is made of a biostable material selected from the group consisting of silicone, polyurethane, polyether urethane, polyether urethane urea, polyamide, polyacetal, polyester, poly(ethylene-chlorotrifluoroethylene), poly tetrafluoroethylene (Teflon), styrene butadiene rubber, polyethylene, polypropylene, polyphenylene oxide-polystyrene, poly-a-chloro-p-xylene, polymethylpentene and polysulfone.

45. The device of claim 31 further comprising a recovery tether attached to the matrix body.

46. The device of claim 31 wherein the analgesic is an analgesic that acts on opioid pain receptors.

47. The device of claim 46 wherein the analgesic that acts on opioid pain receptors is selected from the group consisting of morphine, fentanyl, sufentanil, alfentanil, hydromorphone, meperidine, methadone, buprenorphine, DADL and butorphanol.

48. The device of claim 31 wherein the analgesic is an analgesic that acts on non-opioid pain receptors.

49. The device of claim 46 wherein the analgesic that acts on non-opioid pain receptors is selected from the group consisting of ketorolac, super oxide dismutase, baclofen, calcitonin, serotonin, vasoactive intestinal polypeptide, bombesin and omega-conopeptide.

50. The device of claim 46 wherein the analgesic that acts on non-opioid pain receptors is an alpha-2 adrenergic agonist.

51. The device of claim 48 wherein the alpha-2 adrenergic agonist is selected from the group consisting of clonidine, tizanidine, ST-91, medetomidine and dexmedetomidine.

52. The device of claim 48 wherein the analgesic that acts on non-opioid pain receptors is an NMDA receptor antagonist.

53. The device of claim 52 wherein the NMDA receptor antagonist is selected from the group consisting of dexmethorphan, Ifenprodil and MK-801.

54. The device of claim 48 wherein the analgesic that acts on non-opioid pain receptors is a somatostatin analog.

55. The device of claim 54 wherein the somatostatin analog is selected from the group consisting of Octreotide, Sandostatin, Vapreotide and Lanreotide.

56. The device of claim 31 wherein the body is configured for ease of introduction to and removal from the neuraxis of a body.

57. The device of claim 31 wherein the analgesic is present in the matrix in an amount of about 10% to 80% by weight.

58. The device of claim 31 configured such that the analgesic is eluted at a sustained rate over the useful life of the device.

59. A device for administering an analgesic at a sustained rate over a period of time, the device being shaped, sized and adapted for administering the analgesic into the region of the neuraxis of the analgesic available for diffusion only therefrom in the animal environment into the neuraxis, wherein the analgesic is selected from the group consisting of alpha-2 adrenergic receptor agonists, ketorolac, super oxide dismutase, and serotonin.

60. A device for administering an analgesic at a sustained rate over a period of time, the device being shaped, sized and adapted for administering the analgesic into the region of the neuraxis of an animal environment, the device comprising:

a biostable polymeric matrix body containing an analgesic available for diffusion only therefrom in the animal environment into the neuraxis, wherein the analgesic is selected from the group consisting of alpha-2 adrenergic receptor agonists, ketorolac, super oxide dismutase, and serotonin; and a recovery tether attached to the body.

61. A device for administering an analgesic to an animal at a sustained rate over a period of time, the device being shaped, sized and adapted for administering the analgesic into the region of the spinal column of the animal, the device comprising:

a biostable polymeric hollow tube, the polymeric material capable of allowing a selected analgesic to diffuse only therefrom, the polymeric hollow tube having opposed ends;

the selected analgesic, loaded into the interior of the polymeric hollow tube, the analgesic available for diffusion only therefrom into the region of the spinal column of the animal; and wherein the opposed ends of the polymeric hollow tube are sealed with the selected analgesic inside the tube.

* * * * *